United States Patent [19]

Keeler

[11] 4,191,186

[45] Mar. 4, 1980

[54] REMOVABLE DIGIT ENGAGEABLE MEANS FOR SEPARATING A CATHETER AND STYLET

[75] Inventor: Robert J. Keeler, Wheeling, Ill.

[73] Assignee: Abbott Laboratories, North Chicago, Ill.

[21] Appl. No.: 859,344

[22] Filed: Dec. 12, 1977

[51] Int. Cl.² ................................. A61M 05/00
[52] U.S. Cl. ........................... 128/214.4; 128/221
[58] Field of Search .......... 128/214.4, 215, 348 R, 128/221, 216

[56] References Cited

U.S. PATENT DOCUMENTS

| 2,764,978 | 10/1956 | Everett | 128/215 |
|---|---|---|---|
| 3,312,220 | 4/1967 | Eisenberg | 128/214.4 |
| 3,348,544 | 10/1967 | Braun | 128/214.4 |
| 3,454,006 | 7/1969 | Langdon | 128/214.4 |
| 3,472,232 | 10/1969 | Earl | 128/214.4 X |
| 3,584,624 | 6/1971 | Ciutiis | 128/214.4 |
| 3,677,243 | 7/1972 | Nerz | 128/214.4 |
| 3,714,945 | 2/1973 | Stanley | 128/214.4 |
| 3,856,020 | 12/1974 | Kovac | 128/214.4 X |
| 3,860,006 | 1/1975 | Patel | 128/214.4 X |
| 3,921,633 | 11/1975 | Tischlinger | 128/215 X |
| 3,923,066 | 12/1975 | Francisoud | 128/348 |
| 4,079,738 | 3/1978 | Dunn et al. | 128/214.4 |

FOREIGN PATENT DOCUMENTS

| 181354 | 8/1954 | Austria | 128/214.4 |
|---|---|---|---|
| 1534119 | 7/1968 | France | 128/214.4 |
| 2371204 | 7/1978 | France | 128/214.4 |
| 400463 | 4/1966 | Switzerland | 128/214.4 |
| 448861 | 11/1974 | U.S.S.R. | 128/214.4 |

Primary Examiner—E. H. Eicholt
Attorney, Agent, or Firm—Robert L. Niblack; Aaron L. Hardt; Robert S. Beiser

[57] ABSTRACT

A catheter-outside catheter placement unit wherein the catheter and stylet have connected hubs separable by a removable digit engageable means. Preferably, the removable digit engageable means is carried by a sleeve fitted over the catheter hub.

10 Claims, 11 Drawing Figures

REMOVABLE DIGIT ENGAGEABLE MEANS FOR SEPARATING A CATHETER AND STYLET

BACKGROUND OF THE INVENTION

The present invention relates to catheter placement units and, more particularly, to an easily separable catheter-outside unit.

Catheter placement units of the catheter-outside type are well known in the prior art. Generally, they include an needle or stylet which is pointed at one end and joined to a hub at its other end and a catheter also having a hub at one end thereof. The stylet is inserted into the catheter through the catheter hub until the pointed end of the stylet extends out of the catheter at its other end and the stylet hub is connected to the catheter hub. When the catheter is to be placed into the vein of a patient, the catheter is carried into the vein by the stylet. The stylet is then removed from the catheter and an intravenous fluid infused to the patient through the catheter.

Single-handed separation of the stylet from the catheter is desirable, because it enables the person inserting the catheter to use the other hand to perform other tasks which may need to be performed during separation of the stylet from the catheter. U.S. Pat. No. 3,714,945 granted Feb. 6, 1973 to V. Stanley and entitled "Digit Manipulable Quick Release Cannula Insertion Device" discloses a catheter-outside catheter placement unit which can be separated single-handedly. U.S. Pat. No. 3,348,544 granted Oct. 24, 1967 to B. Braun and entitled "Polypropylene Cannula for Continuous Intravenous Infusion" also discloses a single-handedly separable catheter placement unit.

A disadvantage of the prior art catheters of Stanley and Braun is that their digit engageable means inherently prevent their catheters from being rotated easily when inserted in a patient. Many doctors prefer a rotatable catheter. Accordingly, it is clear that a single-handedly separable catheter-outside catheter placement unit providing a rotatable catheter when inserted would be desirable.

SUMMARY OF THE INVENTION

Therefore, it is the primary object of this invention to provide a catheter-outside catheter placement unit wherein the catheter can be single-handedly separated from the stylet and the catheter is rotatable 360° when inserted in the patient. Another object is to provide a catheter-outside catheter placement unit wherein the digit engageable means for separating the catheter and stylet is disposed substantially at the end of the catheter hub opposite to the end at which the catheter is connected. Still another object is to provide a catheter hub that has an unadorned and uncluttered upper surface when the catheter is inserted in a patient, which allows the catheter hub to be readily taped to the patient's skin.

In accordance with these and other objects, there is provided by the present invention a catheter-outside catheter placement unit having removable digit engageable means associated with the catheter hub for facilitating removal of the stylet from the catheter.

BRIEF DESCRIPTION OF THE DRAWING

Other objects and attendant advantages will be obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
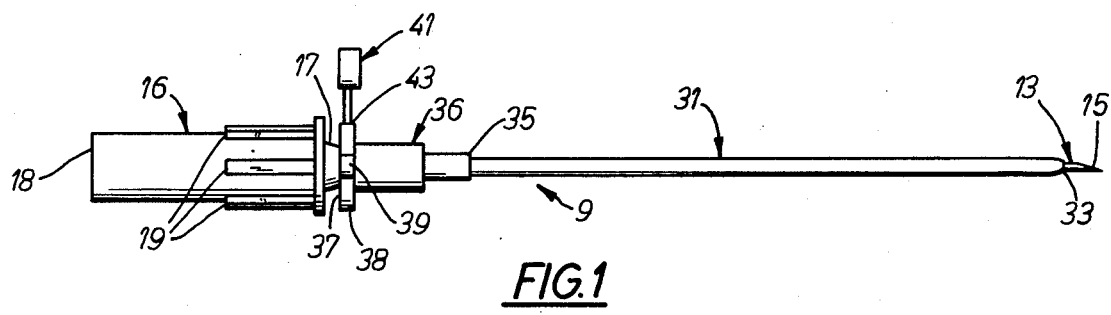
FIG. 1 is a front elevational view of one embodiment of the catheter-outside catheter placement unit of this invention.

Referring to the drawing, there is generally shown in FIG. 1, a catheter placement unit 9. Catheter placement unit 9 includes a stylet 13 having a sharpened first end 15 and a second end embedded in stylet hub 16 having a receiving end 17 of reduced diameter. Stylet hub 16 is preferably a plastic tube, while stylet 13 is a metal tube. When stylet 13 is inserted into a vein, any resultant flashback of blood will be visible in stylet hub 16. Stylet hub 16 can be open or closed at its end 18 and includes finger graspable ridges 19.

Figure 2:
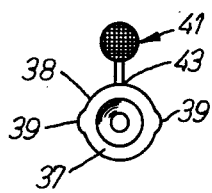
FIG. 2 is a left side elevational view of the catheter of the unit shown in FIG. 1.

Catheter placement unit 9 also includes a preferably plastic catheter 31 slidably disposed or mounted over stylet 13. Catheter 31 has a first end 33 terminating short of the sharpened end 15 of stylet 13. Preferably, end 33 tapers away from sharpened end 15. As seen in FIGS. 1 and 2, catheter 31 has a second end 35 attached to a tubular hub 36 at a first end thereof to provide a continuous flow path from catheter end 33 to the second catheter hub end 37. Preferably, catheter hub 36 is plastic and forms a conventional female Luer fitment having a flange 38 with outwardly extending ears 39 at the catheter hub's second end 37.

When ready for use, catheter placement unit 9 has catheter hub 36 loosely and removably mounted over receiving end 17 of stylet hub 16. After catheter 31 has been carried into a patient's vein by stylet 13, stylet hub 16 and catheter hub 36 can be advantageously single-handedly separated by grasping stylet hub 16 with two or three fingers, while pushing on digit engageable means 41 with the thumb or another finger.

Preferably, digit engageable means 41 can be scored at the plane 43 where it joins flange 38 to facilitate its removal either by pushing or twisting it from catheter hub 36. Alternatively, digit engageable means 41 and flange 38 of catheter hub 36 can have complementary threads by which digit engageable means 41 can be attached to and removed from catheter hub 36.

Figure 3:
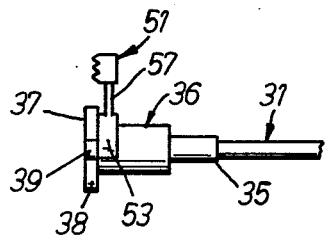
FIG. 3 is a partial front elevational view of another embodiment of the catheter placement unit of this invention.
Figure 4:
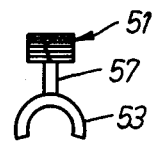
FIG. 4 is a front elevational view of the removable digit engageable means shown mounted on the catheter of FIG. 3.

In FIGS. 3 and 4, there is shown another removable digit engageable means 51 removably mounted on catheter hub 36 by means of a semicircular clasp 53 joined to a stem 57 and friction fitted over catheter hub 36. It will be apparent to those skilled in the art that while digit engageable means 41 has a circular engaging surface and digit engageable means 51 has a rectangular engaging surface, the digit engageable means of this invention can be embodied in any configuration that allows a digit to engage it long enough to force catheter hub 36 from stylet hub 16.

Figure 5:
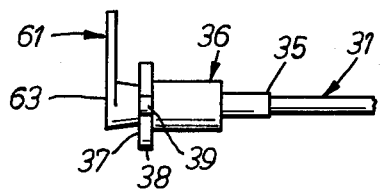
FIG. 5 is a partial front elevational view of another embodiment of the catheter placement unit of this invention.
Figure 6:
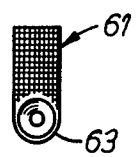
FIG. 6 is a front elevational view of the removable digit engageable means shown inserted into the catheter in FIG. 5.
Figure 7:
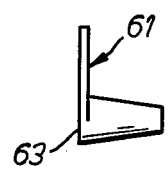
FIG. 7 is a side elevational view of the removable digit engageable means shown in FIG. 6.

In FIGS. 5–7, there is shown another embodiment of the removable digit engageable means 61 of this invention inserted into catheter hub 36 at second end 37 thereof. Digit engageable means 61 has a tubular portion 63 integral therewith which has outer dimensions complementary to the inner dimensions of catheter hub 36. Further, tubular portion 63 likewise has inner dimensions complementary with the dimensions of receiving end 17 of stylet hub 16. Obviously, digit engageable means 61 will be inserted into catheter hub 36 before or concomitant with stylet hub 16.

Figure 8:
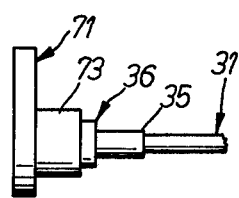
FIG. 8 is a partial front elevational view of another embodiment of the catheter placement unit of this invention.
Figure 9:
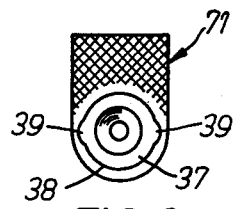
FIG. 9 is a front elevational view of the removable digit engageable means shown disposed over the catheter hub in FIG. 8.
Figure 10:
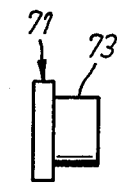
FIG. 10 is a top view of the removable digit engageable means of FIG. 8.

In FIGS. 8–10, there is shown another embodiment of the removable digit engageable means 71 of this invention overlying a portion of catheter hub 36. Digit engageable means 71 has a tubular portion or sleeve 73 which is complementary to catheter hub 36. Advantageously, sleeve 73 protects second end 37 of catheter hub 36 from touch contamination during insertion of catheter 31 into the patient.

Figure 11:
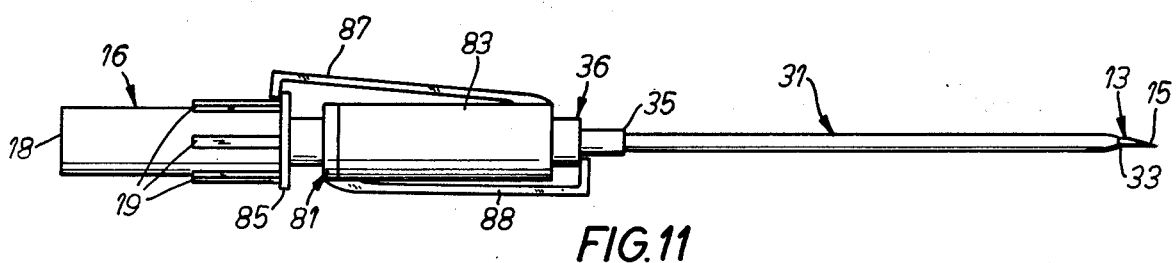
FIG. 11 is a top view of another embodiment of the catheter placement unit of this invention.

In FIG. 11, there is shown an expansion of the embodiment of FIGS. 8–10, shown as digit engageable means 81. Digit engageable means 81 has a tubular portion or sleeve 83 which overlies both catheter hub 36 and stylet hub 16. Preferably, stylet hub 16 has a flange 85 which is closer to end 18 thereof than the flange of stylet hub 16 shown in FIG. 1. Digit engageable means 81 also includes integral spring-like appendages 87, 88 respectively engaging stylet hub 16 and catheter hub 36. It will be apparent to those skilled in the art, that appendages 87, 88 can also both engage stylet hub 16 or catheter hub 36.

Having now described my invention of a removable digit engageable means in specific detail and exemplified several embodiments by which it may be carried into practice, it will be readily apparent to those skilled in the art that innumerable variations, applications, modifications and extensions of the basic principles involved may be made without departing from its sphere or scope.

That which I claim is:

1. In a catheter placement unit including:
    a stylet having a sharpened first end and a second end embedded in a tubular stylet hub having a receiving end of reduced diameter,
    a flexible catheter slidably disposed over said stylet, a first end of said catheter terminating short of said sharpened first end of said stylet and tapering away therefrom and a second end of said catheter attached to a first end of a tubular catheter hub having a second end loosely and removably disposed over said receiving end of said stylet hub, said catheter hub having digit engageable means associated therewith for facilitating removal of said catheter hub from said stylet hub; the improvement which comprises:
    said digit engageable means being removably associated with said catheter hub and removable quickly and easily therefrom by a single handed operation.
2. The catheter placement unit defined in claim 1, wherein said digit engageable means is integrally molded to said catheter hub and includes a weakened portion which facilitates said removal of said digit engageable means from said catheter hub.
3. The catheter placement unit defined in claim 1, wherein said digit engageable means is friction fitted to said catheter hub.
4. The catheter placement unit defined in claim 3, wherein said digit engageable means includes a substantially semicircular clasp having an inner diameter complementary to the outer diameter of said catheter hub.
5. The catheter placement unit defined in claim 3, wherein said digit engageable means includes a tubular portion inserted into said catheter hub at said second end and having outer dimensions complementary to the inner dimensions of said catheter hub at said second end.
6. The catheter placement unit defined in claim 1, wherein said digit engageable means includes a tubular portion fitted over said catheter hub.
7. the catheter placement unit defined in claim 6, wherein said tubular portion further includes an appendage therefrom adapted to be removably affixed to said stylet hub.
8. The catheter placement unit defined in claim 7, wherein said appendages are springs integrally molded to said tubular portion.
9. The catheter placement unit defined in claim 6, wherein said tubular portion further includes an appendage therefrom adapted to be removably affixed to said catheter hub.
10. The catheter placement unit defined in claim 1, wherein said digit engageable means is disposed substantially at said second end of said catheter hub.

* * * * *